(12) United States Patent
Chakrabartty

(10) Patent No.: US 7,757,565 B2
(45) Date of Patent: Jul. 20, 2010

(54) SELF-POWERED SENSOR

(75) Inventor: Shantanu Chakrabartty, Williamston, MI (US)

(73) Assignee: Board of Trustees Operating Michigan State University, East Lansing, MI (US)

(*) Notice: Subject to any disclaimer, the term of this patent is extended or adjusted under 35 U.S.C. 154(b) by 50 days.

(21) Appl. No.: 12/273,844

(22) Filed: Nov. 19, 2008

(65) Prior Publication Data

US 2009/0120200 A1 May 14, 2009

Related U.S. Application Data

(63) Continuation-in-part of application No. 11/895,635, filed on Aug. 24, 2007.

(60) Provisional application No. 60/840,056, filed on Aug. 24, 2006.

(51) Int. Cl.
*G01N 3/32* (2006.01)

(52) U.S. Cl. .......................................... 73/808; 73/777

(58) Field of Classification Search ..... 73/12.01–12.14, 73/760–808
See application file for complete search history.

(56) References Cited

U.S. PATENT DOCUMENTS

| | | | | |
|---|---|---|---|---|
| 4,769,797 | A * | 9/1988 | Murakami | 368/111 |
| 2002/0111756 | A1 * | 8/2002 | Modgil | 702/63 |
| 2008/0047355 | A1 * | 2/2008 | Chakrabartty et al. | 73/808 |

* cited by examiner

*Primary Examiner*—Max Noori
(74) *Attorney, Agent, or Firm*—Harness, Dickey & Pierce, P.L.C.

(57) ABSTRACT

A self-powered sensor is provided for strain-rate monitoring and other low power requirement applications. The self-powered sensor is comprised of: a piezoelectric transducer; a non-volatile memory comprised of at least one floating gate transistor; a current reference circuit adapted to receive a voltage signal from the piezoelectric transducer and operable to output a reference current into the non-volatile memory; an impact-monitoring circuit having a triggering circuit and a switch; the triggering circuit adapted to receive the voltage signal from the piezoelectric transducer and operable to control the switch based on the rate of change of the voltage signal.

25 Claims, 6 Drawing Sheets

SELF-POWERED SENSOR

CROSS-REFERENCE TO RELATED APPLICATIONS

This application is a continuation-in-part of U.S. patent application Ser. No. 11/895,635 filed on Aug. 24, 2007, which claims the benefit of U.S. Provisional Application No. 60/840,056, filed on Aug. 24, 2006. The disclosures of the above applications are incorporated herein by reference.

GOVERNMENT RIGHTS

The U.S. Government may have a paid-up license in this invention, and may have the right, in limited circumstances, to require the patent owner to license others on reasonable terms as identified by the terms of Federal Grant No. CCR-0325571 awarded by the NSF.

FIELD

The present disclosure relates to a self-powered sensor.

BACKGROUND

Approximately 500,000 hip and knee replacements are performed each year in the United States. Although these implants exhibit excellent response during the initial rehabilitation period, fatigue and wear limits their success for long-term operation. Monitoring of fatigue and wear has been previously shown to increase implant longevity by preventing mechanical failure through early intervention. Mechanical fatigue is the accumulation of damage in a structure under applied fluctuating stresses. Though the magnitudes of the applied stresses are less than the tensile strength of the material, the progressive fatigue damage may lead ultimately to mechanical failure. Fatigue life is defined as the number of load cycles necessary to induce failure and it depends on the level of fluctuating strain in the structure. Several fatigue prediction algorithms (e.g. Palmgren-Miner linear rule) rely on counting the number and magnitude of loading cycles applied to a structure. The fatigue in the structure can then be estimated using the cumulative statistics of these applied loads.

Piezoelectric transducers not only provide a mechanism for sensing fatigue in a structure but also can be used for self-powering of the sensors. Piezoelectric based self-powering for medical implants has several advantages over traditional battery powered techniques which suffer from limited life and complications due to biocompatibility. Poly-vinylidene diflouride (PVDF) is a piezoelectric plastic that is currently used for suture materials and has proven to be biocompatible. One disadvantage of PVDF is its very low mechano-electrical energy conversion. Such low power levels pose several challenges for designing self-powered sensors, which include:

1. Self-powered computation: Energy to perform sensing and computation on the sensor has to be harvested from the converted mechanical signal.
2. Non-volatile storage: All the parameters of internal state variables (intermediate and final) have to be stored on a non-volatile memory to account for unavailability of power (i.e. blackouts).
3. Sub-microwatt operation: All computation and storage functions have to be performed at sub-microwatt power dissipation levels to meet the power budget requirement of 1 $\mu$W.

Although many fatigue prediction algorithms mainly rely on the statistics of strain level crossings, it is well known that strain-rates experienced by a mechanical structure also play an important role in predicting fatigue. This is particularly important under high impact conditions during the usage of a biomechanical implant. Thus, it would beneficial to have a self-powered sensor capable of measuring the strain-rates experienced by a mechanical structure.

The statements in this section merely provide background information related to the present disclosure and may not constitute prior art.

SUMMARY

A self-powered sensor is provided for strain-rate monitoring and other low power requirement applications. The self-powered sensor is comprised of a piezoelectric transducer; a non-volatile memory comprised of at least one floating gate transistor; a current reference circuit adapted to receive a voltage signal from the piezoelectric transducer and operable to output a reference current into the non-volatile memory; an impact-monitoring circuit having a triggering circuit and a switch; the triggering circuit adapted to receive the voltage signal from the piezoelectric transducer and operable to control the switch based on the rate of change of the voltage signal.

Further areas of applicability will become apparent from the description provided herein. It should be understood that the description and specific examples are intended for purposes of illustration only and are not intended to limit the scope of the present disclosure.

DRAWINGS

DETAILED DESCRIPTION

Figure 1:
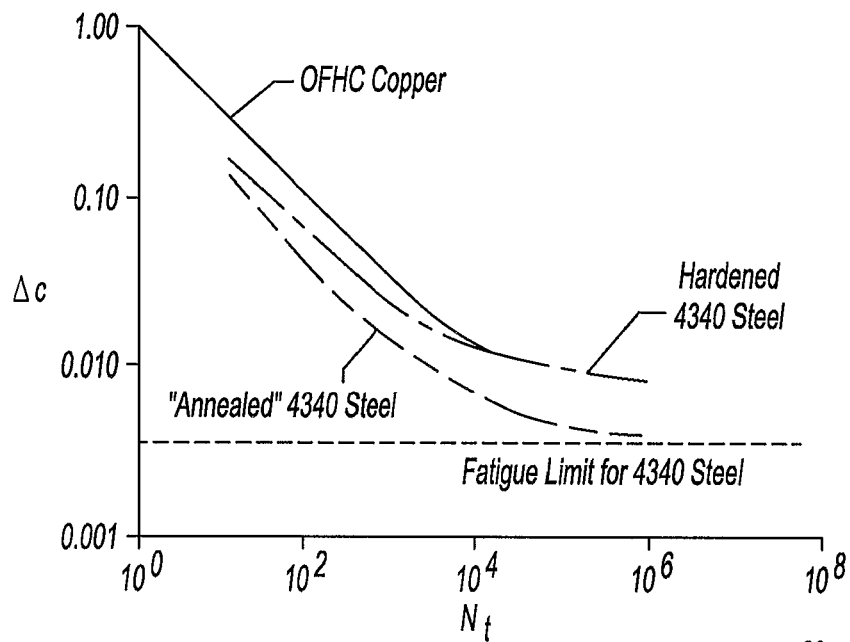
FIG. 1 is an exemplary S-N curve which can be used to estimate fatigue life.

Mechanical fatigue is the accumulation of damage in a structure under applied fluctuating stresses. Though the magnitudes of the applied stresses are less than the tensile strength of the material, the progressive fatigue damage may lead ultimately to mechanical failure. Fatigue life is defined as the number of constant amplitude load cycles necessary to induce failure in an initially undamaged component. Generally, the fatigue life of a mechanical component under cycling applied load depends on the level of fluctuating strain in the structure. With reference to FIG. 1, this can be represented by the S-N curve, which is obtained using experimental measurements. In the S-N curve, S is the mechanical strain level ($\Delta\epsilon$) in the component under a harmonic load, and N is the number of cycles that causes failure of the component at that strain level.

The S-N curves can be used directly to estimate the fatigue life under constant amplitude harmonic load conditions. However, in most applications the applied load is not cyclic. The simplest approach to model fatigue behavior under variable amplitude load condition involves the concept of cumulative damage, which can be described using the Palmgren-Miner linear rule:

$$\sum_{i=1}^{m} \frac{n_i}{N_{fi}} = 1 \quad (1)$$

where $n_i$ denotes total number of events when the electric signal generated by the piezoelectric transducer exceeded a threshold $a_i$. Miner's rule assumes that each strain cycle of a given magnitude consumes $1/N_{fi}$ of the total fatigue life, where $N_{fi}$ is the fatigue life of the specimen at the given strain amplitude (obtained from the S-N curve). A major step in the implementation of this approach is the identification of different loading events that contribute to fatigue damage. Counting algorithms are used to reduce any loading spectra to a series of equivalent stress-strain states. The experimental data for each stress-strain state is implemented with the Palmgren-Miner's rule to provide a summation of fatigue damage. Several empirical cycle counting methods have been developed for different applications. For the purpose of this study, a modified level-crossing peak counting method is used. This method consists of detecting and summing the maximum level reached by different peaks of the applied strain function. It is readily understood that other counting methods may be employed.

Figure 2:
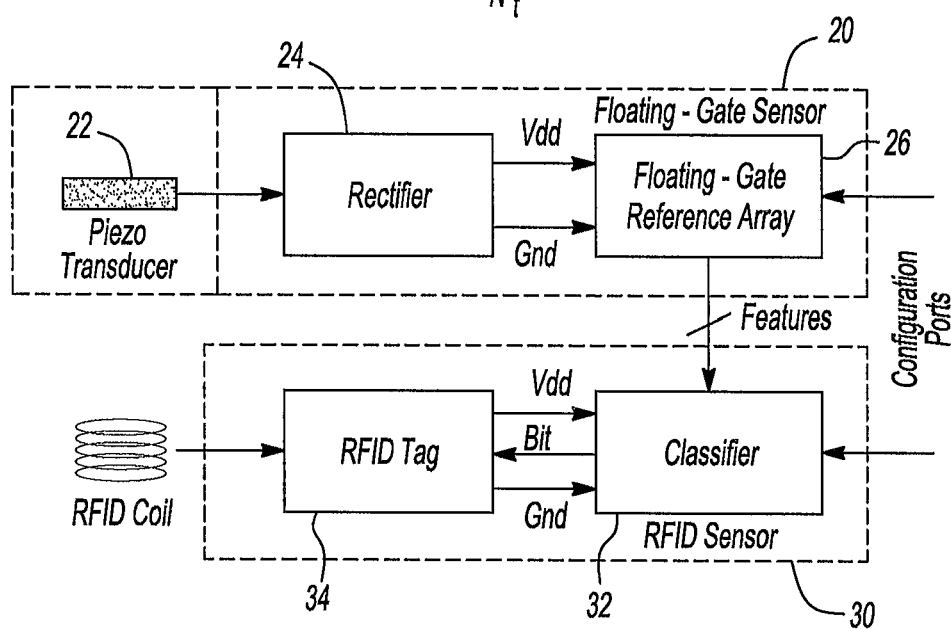
FIG. 2 is a system level architecture of an exemplary fatigue monitoring system.

FIG. 2 illustrates a system level architecture of an exemplary fatigue monitoring system 20. The fatigue monitoring system 20 is comprised of a piezoelectric transducer 22, a rectifier 24 and a floating gate sensor 26. The piezoelectric transducer 22 may be operably coupled to a structure being monitored, such as a medical implant. Stress applied to the monitored object causes the piezoelectric transducer 22 to generate a voltage signal While reference is made throughout this disclosure to medical implants, it is readily understood that the fatigue monitoring system has other applications (e.g., monitoring structural integrity of aircraft or vehicle components).

The floating gate sensor 26 continuously records the output of the piezoelectric transducer 22. The full-wave rectifier 24 interposed between the piezoelectric transducer 22 and the floating gate sensor 26 generates un-regulated supply voltages (vdd and gnd) from the signal output by the transducer 22. In an exemplary embodiment, the full wave rectifier 24 is implemented using a standard diode bridge. For the prototype described below, n+-p-substrate and p+-n-well diodes were used, which naturally occur using electrostatic discharge (ESD) diodes. The supply voltages are used by a floating gate sensor 26 to compute the amplitude and duration statistics of the rectified signal. The floating gate sensor 26 then updates the internal variables which represent cumulative history of the mechanical strain cycles experienced by the monitored structure. The floating gate sensor is self-powered and extracts all its operational energy from the rectified signal.

The floating gate sensor 26 may interface an RFID sensor 30 that is used to interrogate and/or download the recorded statistics. The RFID sensor 30 embeds a classifier 32 that uses the statistics as features to produce a confidence value proportional to time-to-failure. An RFID interface 34 is then used to transmit the confidence value to an external interrogator. The powering and operation of the RFID-subsystem is completely asynchronous and derives its power through RF coupling from an external interrogator.

Figure 3:
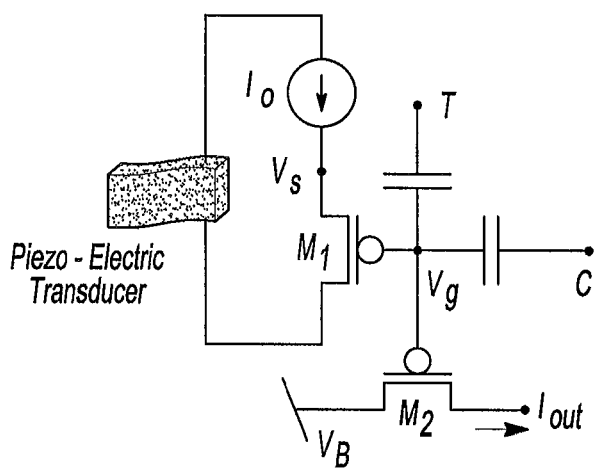
FIG. 3 is a simplified circuit model for a floating gate sensor.

A simplified circuit model for the proposed floating gate sensor 22 is shown in FIG. 3. It consists of a floating gate (denoted by voltage $V_g$) which is coupled to the gates of an injection transistor M1 and a read-out transistor M2. The current delivered by the piezoelectric transducer is limited by a current reference ($I_0$) which biases the transistor M1 in weak-inversion. The nodes C and T represent control and tunneling terminals. In weak-inversion, the expression for source current through the pFET transistor M1 is given by:

$$I_0 = I_s e^{-\kappa \frac{V_g}{U_T}} e^{\frac{V_s}{U_T}}$$

where $I_0$ is the source current, $I_s$ is a pre-exponential current, $V_g$ is the floating gate voltage, K is the coupling coefficient from floating gate to channel, $U_t$ is the thermal voltage. For the fixed reference current $I_0$, the gate current of M1 due to impact ionized hot-electron injection (IHEI) is given by:

$$I_g = \beta I_0 e^{\frac{V_s}{V_{inj}}} = -C \frac{\partial V_g}{\partial t}$$

where $\beta$ and $V_{inj}$ are constants, and C is the total capacitance at the floating gate.

Using equations (1) and (2), the following expression for $V_g$ is obtained as a function of time:

$$V_g(t) = -\frac{1}{K_2} \log\left( K_1 K_2 \left( t + \frac{1}{K_1 K_2} e^{-K_2 V_{g0}} \right) \right)$$

where $$K_1 = \left(\frac{\beta I_0}{C}\right)\left(\frac{I_0}{I_s}\right)^{\frac{U_t}{V_{inj}}}$$

$$K_2 = \frac{\kappa}{V_{inj}}$$

and $V_{g0}$ is the initial gate voltage.

Figure 4:
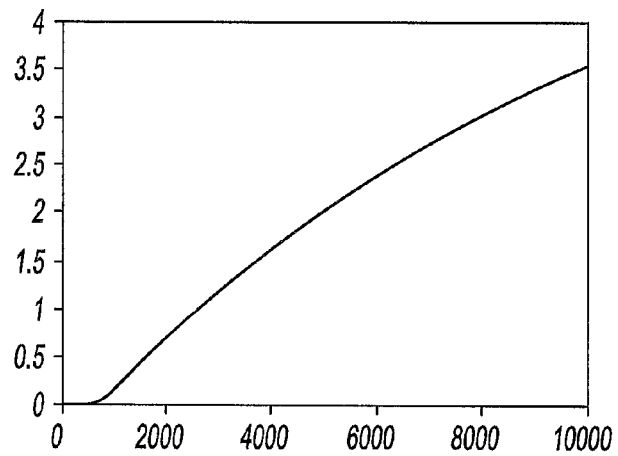
FIG. 4 is a graph of the read out current from a floating gate sensor over time.

The floating gate voltage is mapped onto a read-out current $I_{out}$ using the transistor M2. Because transistor M2 may not be in a weak-inversion we use an EKV model to compute the output current $I_{out}$ as:

$$I_{out} = a^2 \log^2\left(1 + \alpha e^{\frac{-\kappa V_g + V_B}{U_T}}\right)$$

where $\alpha$ and $a$ are parameters of the model. FIG. 4 plots the read-out current $I_{out}$ over time for parameters $\alpha$ and $a$, obtained experimentally. It can be seen from the model that the response of the circuit is monotonic and exhibits a saturating response. Therefore the model in FIG. 3 could be used for calculating the total cumulative time a piezoelectric-transducer was able to deliver a load of current $I_0$, which will be proportional to the cumulative stress period applied to the implant.

Figure 5:
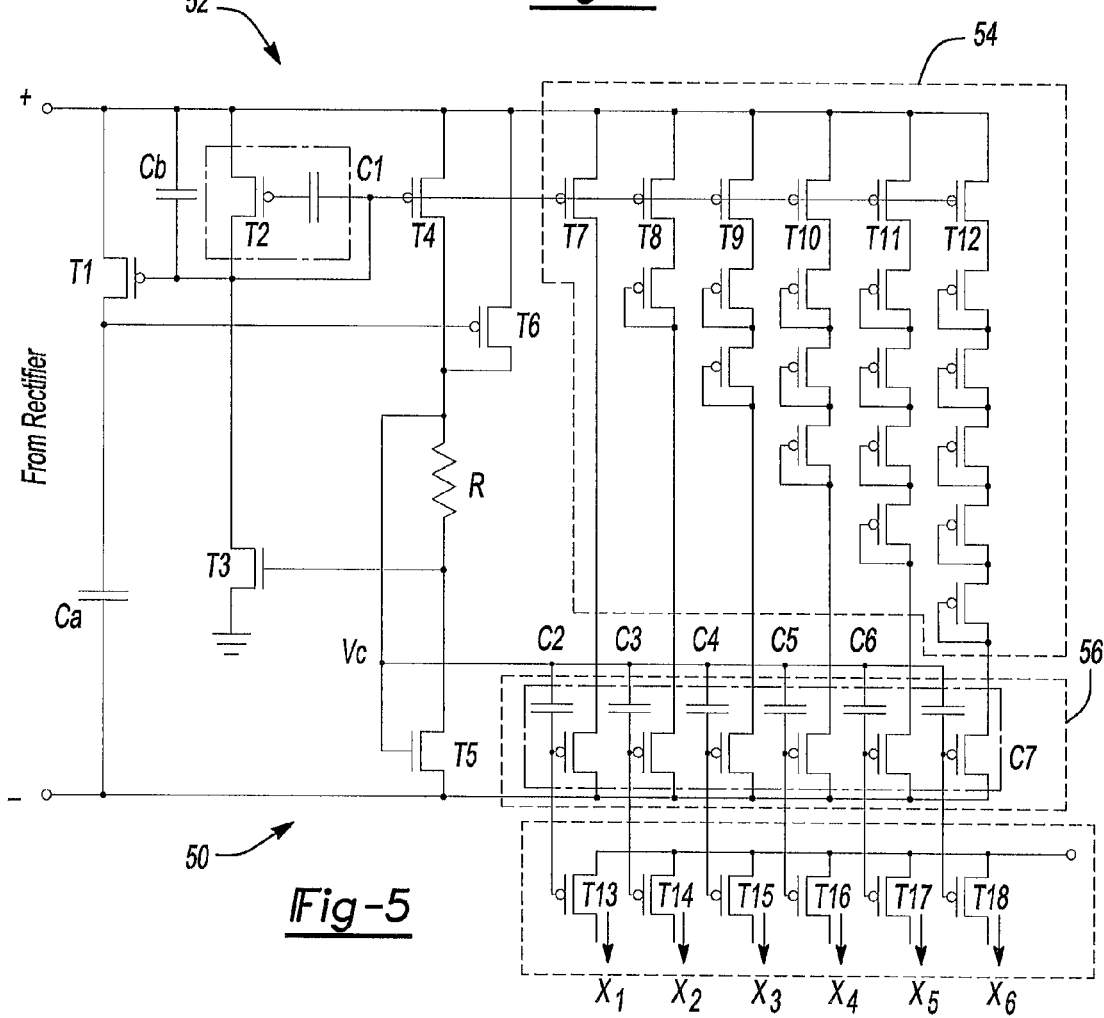
FIG. 5 is a schematic of an exemplary implementation of a floating gate sensor.

FIG. 5 illustrates an exemplary implementation of a floating gate sensor 50. The floating gate sensor 50 is comprised of a current reference circuit 52, a driving circuit 54 and a storage circuit 56. Each of these circuits is further described below.

In an exemplary embodiment, the reference current circuit 52 is implemented using transistors T1-T5 and resistor R. In a standard current reference circuit, the ratio of the pMOS current mirror transistors along with R determines the magnitude of the reference current. This exemplary implementation uses a floating gate transistor T2 coupled to a gate of transistor T1. The reference current is determined by the charge injected onto the floating gate T2 and the resistor value R. When all the transistors T2-T5 are biased in weak-inversion (i.e., operating in a sub-threshold mode), the reference current through T4 is given by $$I_{ref} \approx \frac{Q_f}{C_f R}$$

where $Q_f$ is the charge stored on the floating gate C1 and $C_f$ is the total floating gate capacitance. By accurately controlling the amount of floating gate charge, $Q_f$, small increments of reference current can be generated. The charge on the gate can be modified using hot electron injection or through tunneling. Injection adds electrons to the floating gate as a result its potential decreases which leads to an increase in the drain current through the transistor. For a pMOS transistor biased in weak-inversion drain-to-source voltages greater than 4.5V has been found to be sufficient for injection. Of note, the current reference circuit is able to compensate for temperature variations, as evident from reference current expression which is independent of temperature dependent parameters. Temperature compensation due to the current reference circuit has been validated through simulation and exhibits less than 2% variation over a 70° C. variation in temperature. Even though this feature is not required during normal operation of the implantable device, it has been observed that for some implants (hip implants) repeated wear and tear can dramatically increase in ambient temperature. While a particular circuit configuration was described above, it is readily understood that other circuit configurations, preferably having at least one floating gate transistor, may be used for the current reference circuit.

In the exemplary embodiment, a storage capacitor $C_a$ was used at the output of the rectifier to filter out unwanted high-frequency components. The size of the capacitor provides a trade-off between total discharge time versus the voltage swing at the sensor. For the prototype an external capacitor (10 nF) was chosen which led to voltage swing of up to 8V for 20V generated by the piezoelectric transducer. A voltage over-protection and clamping circuitry was integrated at the output of the diode bridge to prevent damage due to unwanted piezoelectric surges.

The storage circuit 56 is an array of floating gate transistors C2-C6 which provide non-volatile storage. A floating gate is a poly-silicon gate surrounded by an insulator, which in standard semiconductor fabrication process is silicon-dioxide. Because a floating gate is surrounded by high quality insulation any electrical charge injected onto this gate is retained for long intervals of time (>8 years). In the exemplary embodiment, each floating gate transistor C2-C6 also has a tunneling capacitor which is used for removing electrons (erase operation) from the gate. It is envisioned that other types of storage circuits are within the broader aspects of this disclosure.

An exemplary driving circuit 54 is interposed between the current reference circuit 52 and the array of floating gate transistors 56. In this exemplary circuit, transistors T7-T12 mirror the current in T4 to drive the floating gate transistors C2-C7. More specifically, the driving circuit is comprised of a plurality of circuit branches, where each circuit branch electrically couples to a different floating gate transistor in the array of floating gate transistors. Voltage drop in each branch will be controlled using diode connected pMOS transistors and will ensure different drain-to-source voltage across each of floating gate cells C2-C7. During the pre-calibration stage each of the floating gate cells are programmed (using tunneling and injection) to store a fixed amount of charge, hence a fixed gate voltage across C2-C7. When a rectified voltage is presented across the supply terminals (+−), the circuit generates a reference current and a stable voltage reference at node Vc. Depending on the magnitude of the rectified voltage, different cells C2-C7 start injecting charge on its floating gate. Likewise, other circuit configurations are envisioned for the driving circuit.

Figure 6:
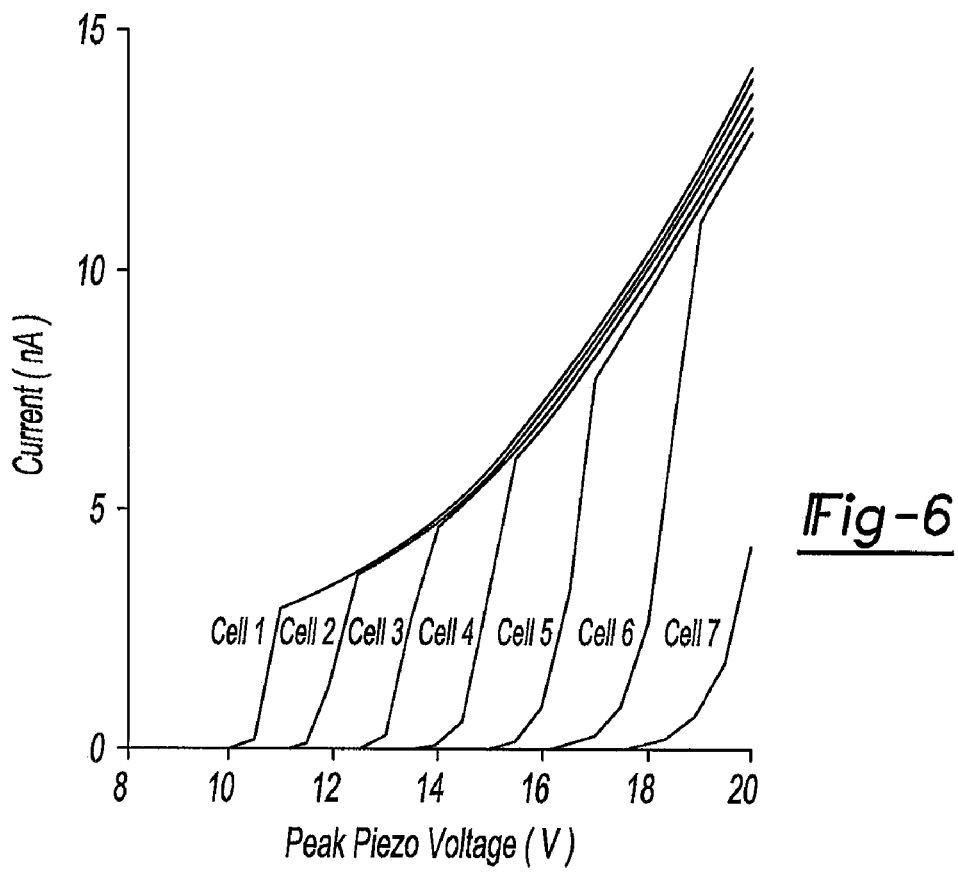
FIG. 6 is a graph illustrating simulation results obtained using the floating gate sensor.

SpectreS based spice simulation of the current reference circuit demonstrates an activation profile of different floating gate cells C2-C7 at different peak amplitude as show in FIG. 6. For this experiment a storage capacitor of 10 nF was chosen, and the duration of the piezoelectric pulse excitation was set to 2 seconds. The circuit exhibits a start-up time of 100 ms, which is sufficient for most structural engineering applications. The start-up however can be optimized by appropriately sizing the storage capacitor at the rectifier but at the expense of lower coupling voltage (rectifier). The simulation also shows poor current regulation of the reference circuit due to sub-threshold operation of the circuit but does not adversely affect the response of the sensor.

The results indicate that different floating gate cells in the array start injecting at different piezoelectric potential and therefore record cumulative amplitude statistics of a signal. The architecture therefore implements a self-powered flash data converter. The total charge accumulated on the floating gate is measured by sensing the current through the read-out transistors T13-T18. The transistors T13-T18 act as read-out transistors that are used to quantify the stored charge on floating gates C2-C7 by measuring the drain currents flowing through T13-T18. The read-out transistors are powered by an external interrogator by transferring energy via physical inter-connections or via RF coupling. Thus, the sub-circuit enclosed in the dotted line in FIG. 5 is to be implemented in the RFID sensor subsystem in FIG. 2. The drain currents through transistors T13-T18 represents a feature vector encoding the history of stress-strain patterns and is used by a classifier to generate time-to fail confidence scores.

A prototype floating-gate sensor was fabricated in a standard 0.5 μm CMOS process. The floating gate transistors were designed using a double polysilicon transistor with a minimum injection potential of 4.2V and an erase voltage of 15V. For preliminary experiments, a signal generator was used to simulate the functionality of a piezoelectric transducer. Different voltage levels were applied at the floating gate array input and the read-out current through transistor T13 was measured.

Figure 7:
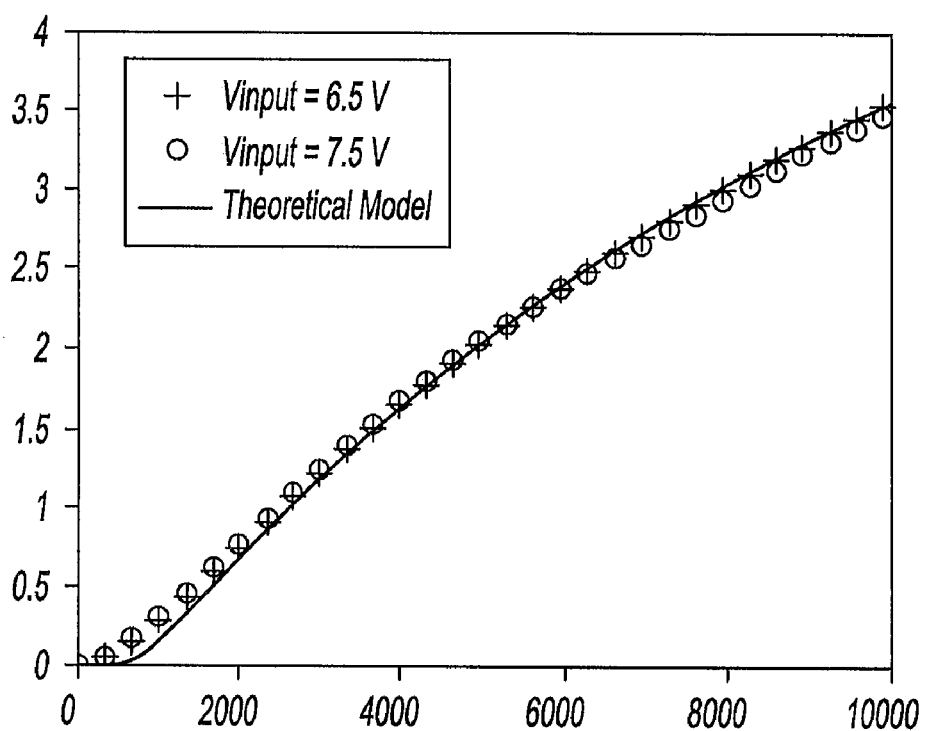
FIG. 7 is a graph depicting the measured response of the single floating gate reference element.

FIG. 7 shows the current measured through transistor T13 for different voltages against the total duration of the applied input. The injection profiles for different voltages are relatively close to each other due to current reference based injection architecture. The response is monotonic and approximately linear which demonstrates that the sensor can be used for computing total strain cycles experienced by a mechanical structure. The total power dissipated during the entire experiment was measured to be 320 nW which is well below the power generated by a PVDF transducer (1 μW). For long term monitoring it is critical that the measured current show a compressive non-saturating response (equivalent to logarithmic response). Long term monitoring experiments with the floating gate sensor have shown non-saturating response for up to $10^5$ seconds demonstrating the effectiveness of current limiting transistors T7 in FIG. 5.

In this disclosure, embodiments of a self-powered fatigue measuring system based on a combination of piezoelectric transduction and floating gate injection was demonstrated. Preliminary results indicate that the response of the sensor is proportional to an equivalent total number of stress cycles experienced by a structure. The total power dissipation of the sensor is less than 1 μW. The above description is merely exemplary in nature and is not intended to limit the present disclosure, application, or uses.

In a second embodiment, the circuitry of a fatigue monitoring circuit may be modified so that the self-powered sensor can act as a long term strain rate monitor. Although many fatigue prediction algorithms mainly rely on the statistics of strain level crossings, it is well known that strain-rates experienced by a mechanical structure also play an important role in predicting fatigue. This is particularly important under high impact conditions during the usage of a biomechanical implant. In the following embodiment, a self-powered sensor capable of reporting statistics of the rate of the strain change inside a given structure is described. Although the internal circuitry differs from the sensor described above, the framework is similar to that described above, as power is harvested using the strain on a given piezoelectric transducer and strain rate statistics are recorded using the harvested energy.

As described above, the sensor directly harvests power from the strain itself. This is challenging because a piezoelectric transducer only generates nanowatts of power. The proposed circuitry allows the sensor to operate on the relatively small amount of power harvested from the piezoelectric transducer.

Figure 8:
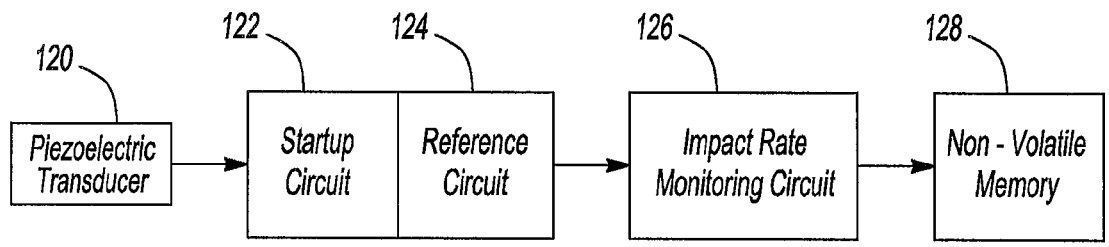
FIG. 8 is a system level architecture of an exemplary strain rate monitoring system.

FIG. 8 illustrates a system level architecture of an exemplary long term strain rate monitoring sensor. The strain rate monitoring sensor is comprised of a piezoelectric transducer 120, a startup circuit 122, a reference circuit 124, an impact rate monitoring circuit 126 and a non-volatile memory 128. The piezoelectric transducer 120 may be operably coupled to a structure being monitored, such as a medical implant. Stress applied to the monitored object causes the piezoelectric transducer 120 to generate a voltage signal. As the stress varies, the voltage signal varies accordingly. The rate at which the voltage signal varies is, therefore, proportional to the rate at which strain is applied to the sensor varies. Thus, the strain rate monitoring sensor measures strain rate statistics by measuring the rates at which the voltage signal varies. The floating gate sensor may interface an RFID sensor (not shown) or another device that is used to interrogate and/or download the recorded statistics, details of which are described above. While reference is made throughout this disclosure to medical implants, it is readily understood that the fatigue monitoring system has other applications (e.g., monitoring structural integrity of aircraft or vehicle components).

Strain rate monitoring sensor continuously measures the rate of strain placed on piezoelectric transducer 120. As the amount of strain placed on piezoelectric transducer 120 varies, the voltage produced by transducer 120 will also vary. As the voltage signal varies, startup circuit 122 enables the reference circuit to generate a reference current having stable state. Reference circuit 124 mirrors the stable reference current and supplies the reference current to impact rate monitoring circuit 126. The impact rate monitoring circuit is designed such that when the frequency of the voltage signal exceeds a certain threshold, a triggering circuit drives a switch in the impact rate monitoring circuit, which allows the reference current to flow from reference circuit 124 to the non-volatile memory 128, which continuously injects electrons or charge into a floating gate transistor for as long as the switch is closed. Once the rate of change decreases below the predefined frequency, the injector is once again starved of current and the injection process ends. The total amount of time that the strain rate exceeds a predetermined threshold is proportional to the amount of electrons or charge stored in non-volatile memory 128.

Figure 9:
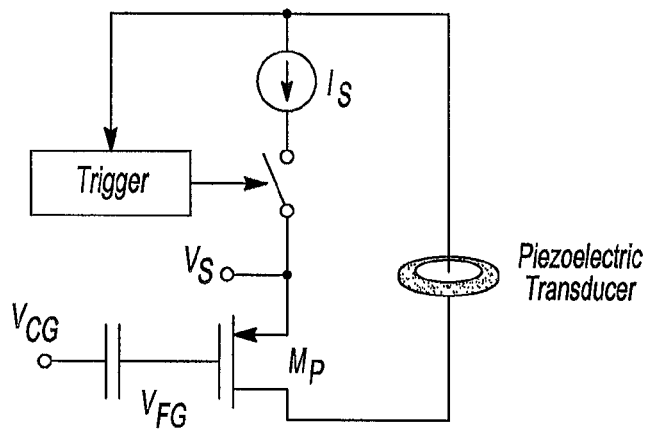
FIG. 9 is a simplified circuit model for a floating gate sensor.

The operation of the proposed impact rate monitor is illustrated using the schematic shown in FIG. 9. It consists of the current starved floating-gate injection circuit FG that was discussed above. The circuit consists of a pMOS floating-gate transistor $M_p$ which is connected to a constant current source $I_S$. The gate of transistor $V_{FG}$ is completely insulated by silicon-di-oxide. Thus, the floating-gate injection circuit acts as a non-volatile memory. As a result, electrons injected onto the node are retained for a long period of time. For impact-rate monitoring, triggering circuit TC controls a switch SW which allows the reference current $I_S$, to flow through the injector. When the voltage generated by the piezoelectric transducer is sufficiently high (typically >4.2V in a 0.5 um CMOS process), and the switch is ON, IHEI starts and electrons are injected onto the floating-gate.

Figure 10:
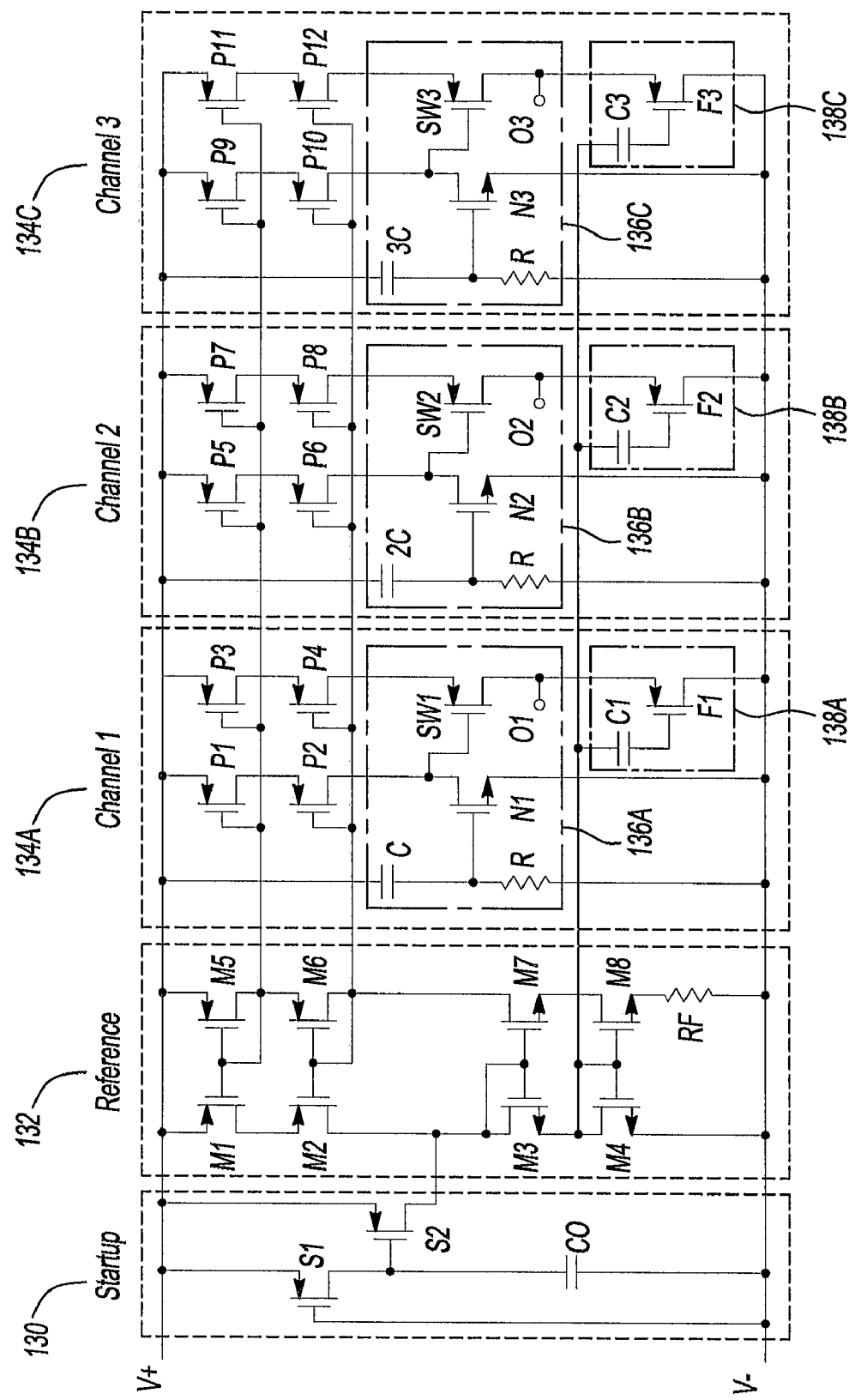
FIG. 10 is a schematic of an exemplary implementation of a strain rate sensor.

FIG. 10 depicts an exemplary embodiment of the schematic of the impact rate monitor 130. Impact rate monitor is comprised of a piezoelectric transducer (not shown), startup circuit 130, reference circuit 132, and at least one impact monitoring circuit 134A-134C.

When a strain or force is exerted on the piezoelectric transducer of the impact rate monitor, startup circuit 130 initializes reference circuit 132 whereby the reference current flowing from reference circuit 132 jumps from one stable point, $I_{rc}$32 0, to a second stable point, where $I_{rc}$ is equal to some constant value, independent of voltage. Put another way, the current reference circuit has two stable states, one state where the reference circuit 132 conducts no current and a second stable state where the reference circuit conducts a reference current. Startup circuit 130 is implemented so that the reference circuit is always in one of the two states. The drain of transistor S1 is connected to $V_+$ and $V_-$ is connected to the gate of transistor S1. Capacitor C0 is connected to the source of transistor S1. The intermediate node between capacitor C0 and transistor S1 is the gate of S2. Exemplary startup circuit 130 is comprised of two p-type transistors S1 and S2 and capacitor C0. Thus, when the piezoelectric transducer produces a voltage potential and power is available, transistor S1 is on and will charge C0 until C0 is charged. While C0 is charging, S2 will drive the gate of M3 by injecting additional current at the startup. Once C0 is charged, then startup circuit 130 is switched off.

Reference circuit 132 can be a standard reference circuit. Reference circuit 132 is comprised of two current mirrors, the first current mirror is comprised of transistors M1 and M5 and the second current mirror is comprised of transistors M4 and M8. The reference current is determined by the size of transistor M1 and M5 (e.g. M1=60 µm/10 µm, M5=30 µm/10 µm) and the value of resistor RF (e.g. 1.5 MΩ). Transistors M3 and M7 and transistors M2 and M6 may be optionally used to improve the performance of the reference circuit 132. The reference circuit 132 supplies current to the floating gate injectors F1-F3 of the impact monitoring circuits 134A-134C. It is understood that the above-described reference circuit is merely an exemplary embodiment and that a number of alternative embodiments may be used as a reference circuit.

Exemplary impact monitoring circuits 134A-134C consist of current copiers P1 and P2, P3 and P4, P5 and P6, P7 and P8, P9 and P10, and P11 and P12, a triggering circuit 136A-136C for each impact monitoring circuit 134A-134C, and a floating gate injection circuit FC connected to each triggering circuit and operable to receive a reference current from current copiers P3 and P4, P5 and P6, and P11 and P12. Each current copier P1-P12 is comprised of two p-type transistors receiving the reference current from the current mirror of reference circuit 132. The current copiers are used to provide the amplifiers N1-N3 and floating gate injectors 138A-138C with identical currents corresponding to the reference current. It is understood to those having skill in the art that alternative embodiments of current copiers exist and may be used interchangeably.

The triggering circuits 136A-136C are individually compromised of a high-pass filter formed by resistor R and capacitor C-3C (commonly referred to as an R-C bridge), common source amplifiers N1-N3 connected at the intermediate nodes of the R-C bridges, and switches SW1-SW3.

The impact monitoring circuits 134A-134C are configured such that impact monitoring circuits 134A-134C may begin receiving current at different rates. While FIG. 10 depicts an embodiment having three impact monitoring circuits channels 134A-134C, it is understood that a self-powered circuit may have more or less than three impact monitoring circuit channels. Each triggering circuit 136A-136C has a high-pass filter operable to filter out a specific frequency. When the rate of change of the voltage signal produced by the piezoelectric transducer exceeds a predetermined threshold, current will flow from V+ and V− through the high pass filter, thereby biasing the gate of a common source amplifier N1-N3. By choosing capacitors C-3C with different capacitances (e.g. 5, 10 and 15 nF respectively), each high-pass filter will begin operating at a different frequency (10 Hz, 5 Hz and 2.5 Hz respectively). Capacitors C-3C for the triggering circuits are all located off-chip due to their relatively large size. Common source amplifiers N1-N3 are n-type transistors that serve as comparators and operate to drive switches SW1-SW3. The sources of common sources of amplifiers N1-N3 are connected to the current copiers and their drains are connected to V−. Unlike the high-pass filters, which do not receive the reference current, the common source amplifiers N1-N3 receive a reference current when the gate of the amplifier is sufficiently biased. When a high-pass filter receives a sufficient voltage signal, current flows from V+ to V− via the high pass filter. The current flowing through the high-pass filter biases the gate of common source amplifier N1-N3, which drives a switch SW1-SW3. Switches SW1-SW3 are p-type transistors that allow the reference current to flow to the floating gate injection circuit 138A-138C when switch SW1-SW3 is closed. It is envisioned that alternative embodiments of the triggering circuit may be used in building the disclosed self-powered strain-rate sensor.

Once the switch is closed, a charge may be injected into floating gate injection circuit 138A-138C, which may be comprised of transistors F1-F3 and capacitors C1-C3. The floating gate injection circuit 138A-138C is a storage circuit. The charge is supplied by the reference current received from reference circuit 132. Floating gate injection circuits 138A-138C are collectively an array of floating gate transistors which provide non-volatile storage. A floating gate is a polysilicon gate surrounded by an insulator, which in standard semiconductor fabrication process is silicon-dioxide. Because a floating gate is surrounded by high quality insulation any electrical charge injected onto this gate is retained for long intervals of time (>8 years). In the exemplary embodiment, each floating gate transistor also has a tunneling capacitor C1-C3 which is used for removing electrons (erase operation) from the gate. The floating gate injectors are operating in weak-inversion mode. The presented floating injection circuit is merely an exemplary embodiment. It is envisioned that other types of storage circuits are within the broader aspects of this disclosure.

Figure 11:
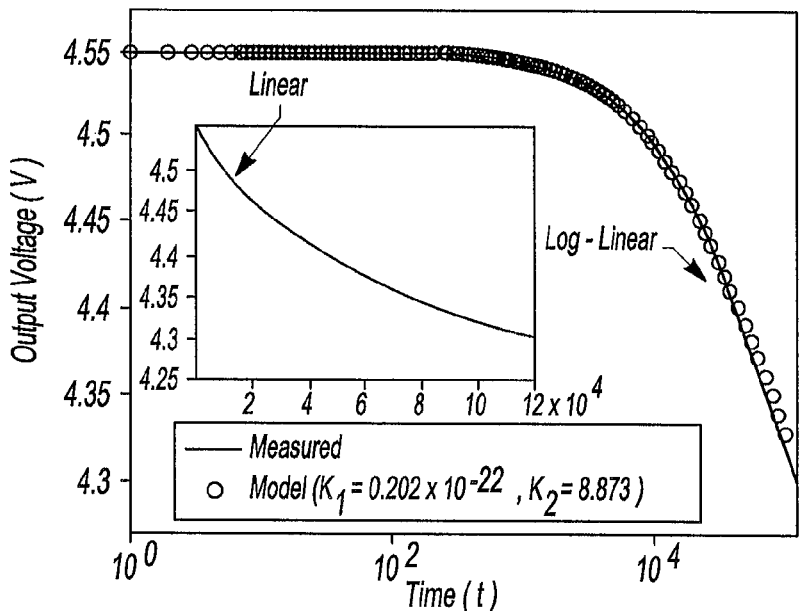
FIG. 11 is a graph of a mathematical and measured responses of IHEI plotted on a logarithmic scale and a linear scale (inset)

If T denotes the set of time intervals during which the triggering is enabled, then the source voltage $V_s$, can then be expressed as $$V_s = \frac{1}{K_2} \log\left(K_1 K_2 \int \partial \tau + e^{-K_2 V_{SO}}\right) \quad (1)$$

with $$K_1 = \frac{\kappa \beta I_S}{C_t}, K_2 = \frac{1}{V_{inj}}$$

where K is the floating-gate efficiency, $C_t$ is the total capacitance of node $V_{FG}$, $\beta$ and $V_{inj}$ are injection parameters which only depend on the aspect ratio of the transistor and the CMOS process. FIG. 11 plots the voltage $V_s$, according to equation (1) with respect to the total triggering duration and compares it with measured result obtained from a fabricated prototype in a 0.5-µm CMOS process. The measured response is shown to be in close agreement with the mathematical model in equation (1). Under the condition when the total triggering duration satisfies $$\int_{\tau \in T} d\tau \ll e^{K_2 V_{SO}} / K_1 K_2,$$

a linear response of $V_s$ with respect to t is obtained. This region is highlighted in the FIG. 12 inset and is useful for short-term monitoring. For the condition $$\int_{\tau \in T} d\tau \gg e^{K_2 V_{SO}} / K_1 K_2^1,$$

equation (1) can be approximated by a log-linear response as:

$$V_S = -\frac{1}{K_2}\log(K_1 K_2) - \frac{1}{K_2}\log\left(\int \partial \tau\right) \quad (2)$$

where $\tau \in T$.

The log-linear response shown in FIG. 2 is important for long-term impact monitoring applications. The first part of equation (2), $$-\frac{1}{K_2}\log(K_1 K_2),$$

denotes an offset which is dependent on biasing and initialization conditions, where as the second part in equation (2), $$-\frac{1}{K_2}\log\left(\int \partial \tau\right)$$

is a log-linear function of the total triggering duration and is scaled by the parameter $K_2$.

The floating-gate injectors have a robust response to mismatch and variations in biasing conditions. For instance, the variation in the parameter $K_2$, was measured to be less than 10% when the bias current was varied by more than 100%. This result is encouraging because it implies that the precision of the source current is not critical for the operation of the injector. The variation in the parameter $K_2$ for different injectors (located on different silicon dies but from the some fabrication run) was found to be less than 15%. Thus, by operating the injector in a differential manner, the offset in equation (2) can be eliminated where the response can be expressed only as a function of $K_2$ and the total triggering duration as:

$$V_S = \frac{1}{K_2}\log\left(\frac{t_0 + \partial \tau}{t_0}\right)$$

where $t_o$ denotes a reference time with respect to which the triggering duration is measured.

Before the sensor can be used for monitoring, all the outputs of the floating-gate injectors (01-03) are first equalized to the same potential. The equalization procedure is similar to the method presented above, where an injector to be initialized is first selected. The input terminals V⁺ and V⁻ are then connected to 5.5V and the floating-gate transistor is injected till the output voltage 01-03 reaches 4.8V. This potential is sufficient to initiate an IHEI process when the channel is triggered by enabling the switches SW1-SW3.

Figure 12:
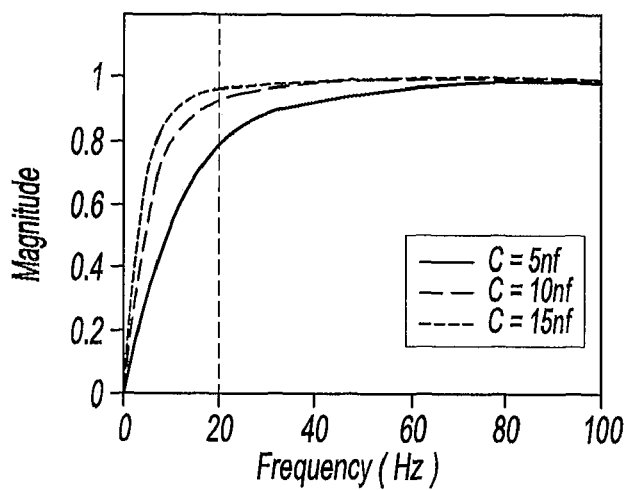
FIG. 12 is a graph of the injection responses for the impact with different rising speeds.
Figure 13:
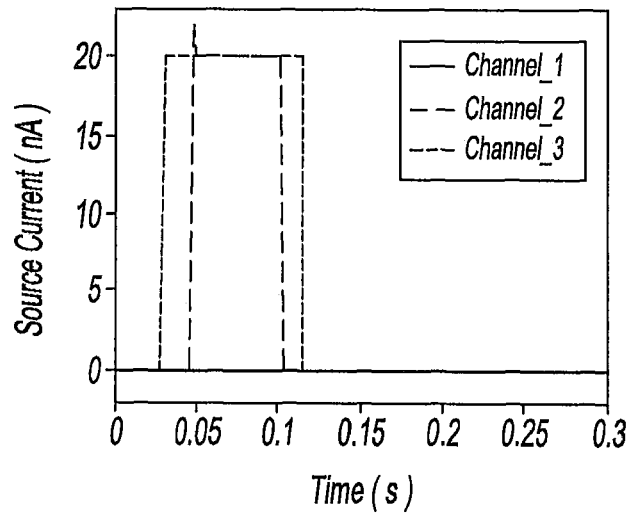
FIG. 13 is a second graph of the injection responses for the impact with different rising speeds.

When the voltage level produced by the piezoelectric transducer exceeds a threshold voltage (3.3V), reference circuit 132 initializes all the current biases. For the circuit in FIG. 10 and parameters given in Table 1, the startup time for the current reference is 30 ms. The startup time determines the upper bound of the impact rates that can be measured using the sensor. This was found to be <35Hz which is within the range of most biomechanical impact rates (1 Hz-50 Hz). Based on the rate of change of the supply voltages V⁺ and V⁻, the bandwidth of the high-pass filter determines the amplitude of the signal presented at the input of the comparator N1. When the signal amplitude exceeds the threshold of the comparator (determined by the bias current), the switches SW1-SW2 are triggered (active "low") and as a consequence the injectors F1 and F2 record the occurrence of the impact. FIG. 12 shows the AC response of the filters whose low-frequency cut-offs have been set to 10 Hz, 5 Hz and 2.5 Hz. This ensures that impact monitor circuit IMC1 triggers only for a slow varying input signal (slowly changing impact). However, all the impact monitor circuits 134A-134C trigger for a fast varying input signal (high impact rates). FIG. 13 shows the triggering event for the three impact monitor circuits, when channel 1 is not triggered where as channel 2 and 3 are triggered. Note that the duration of the triggering is different for channel 2 and 3 implying that channel 3 will inject for a longer duration compared to channel 2.

Figure 14:
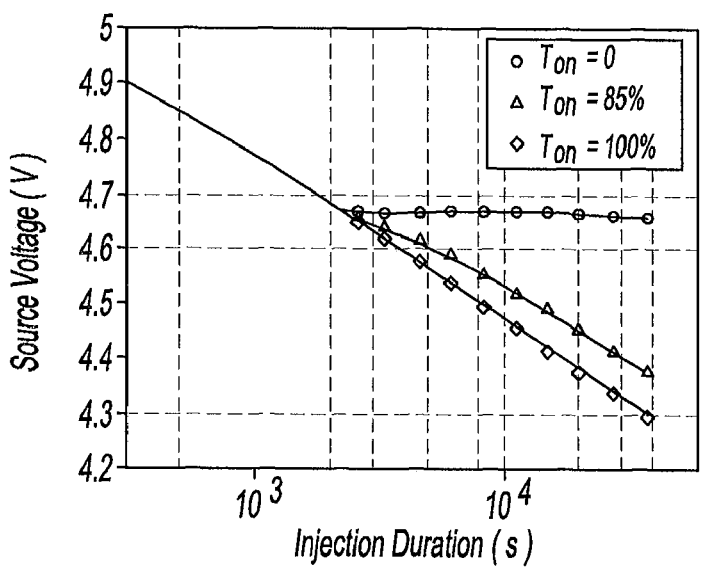
FIG. 14 is a graph of measurements when a prototype sensor is subjected to different durations proportional to impact rate.

Even though the floating-gate injectors are equalized by programming the output voltage 01-03 to 4.8V, the procedure is still prone to initialization errors. We compensate for these errors by using a calibration procedure based on the differential response of the injector as given by equation (3). All the channels are first allowed to inject for a reference duration $t_o$ such that $t_o \ll e^{K_2 V_{S0}}/K_1 K_2$. This ensures that the initialization errors and biasing errors are fully calibrated before the sensor is used for monitoring. FIG. 14 shows the calibration procedure where all the three channels are injected for a duration of $t_0 = 3000$ s. It can be seen that at the end of 3000 cycles, the initialization errors for all the three channels have been calibrated.

After the calibration procedure, the fabricated prototype was subjected to different impact rates which were synthetically generated using a programmable signal generator. An equivalent input voltage (emulating the transducer output) to the prototype was 6.1 V. The impact rates (based on the RC time-constant) were chosen such that channel I did not inject, where as channel 2 injected for only 85°/a of the duration and channel 3 injected for 100% of the duration. FIG. 14 shows that the sensor is able to distinguish different impact-rate levels, where the offset in the log-linear response is directly proportional to the relative triggering duration (calculated with respect to the total observation period). Even though FIG. 14 shows the operation of the sensor up to 40000 cycles (seconds), we have verified its functionality beyond $10^5$ cycles.

The embodiment described above describes a nanowatt integrated circuit that can harvest power from a piezoelectric transducer to monitor strain rates experienced by a structure. The sensor is based on a novel integration of a triggering circuit with a piezoelectric-floating gate injector and can operate for more than 1,000,000 load cycles. The sensor integrates computation and storage within a single device that can have a size of 1.5 mm×1.5 mm and can be imbedded inside structures for autonomous monitoring and fatigue sensing. The above description is merely exemplary in nature and is not intended to limit the present disclosure, application, or uses.

In an alternative embodiment, the piezoelectric transducer may be in the form of a piezoelectric film. The piezoelectric film may be connected to the circuitry presented above. The piezoelectric film may be configured to fit on a tamperproof cap or packaging so that tampering may be detected even in the absence of a seal being broken.

What is claimed is:

1. A self-powered sensor comprising:
   a piezoelectric transducer;
   a non-volatile memory
   a reference circuit, the reference circuit adapted to receive
      a voltage signal having rate of change from the piezoelectric transducer and operable to output the reference current into the memory;

an impact rate monitoring circuit including a switch and a triggering circuit;

the switch interposed between the reference circuit and the memory; and the triggering circuit adapted to receive the voltage signal from the piezoelectric transducer and operable to control the switch based on the rate of change of the voltage signal.

2. The self-powered sensor of claim 1 wherein the triggering circuit is operable to close the switch when the rate of change of the voltage signal exceeds a predefined threshold.

3. The self-powered sensor of claim 1 wherein the triggering circuit includes a high-pass filter sensitive to the rate of change of the voltage signal.

4. The self-powered sensor of claim 3 wherein the triggering circuit further comprises an amplifier interposed between the high-pass filter and the switch.

5. The self-powered sensor of claim 4 wherein the amplifier is configured as a comparator and is operable to drive the switch when the high-pass filter determines that the voltage signal has exceeded the predefined threshold.

6. The self-powered sensor of claim 1 wherein the piezoelectric transducer is operable to power the self-powered sensor.

7. The self-powered sensor of claim 1 wherein the non-volatile memory is comprised of an array of floating gate transistors.

8. The self-powered sensor of claim 7 wherein the reference circuit is operable to inject a charge onto different floating gate transistors of the array based on the rate of change of the voltage signal.

9. The self-powered sensor of claim 8 wherein the impact monitoring circuit is comprised of a plurality of channel circuits, where each channel circuit is operable to inject a charge into different floating gate transistors of the array based on the rate of change of the voltage signal.

10. The self-powered sensor of claim 9 wherein each circuit branch defines a different voltage rate threshold, whereby charge is injected into the floating gate transistor associated with a given channel circuit when the magnitude of the reference current exceeds the voltage change rate threshold for a given channel circuit.

11. The self-powered sensor of claim 1 further comprising a startup circuit interposed between the piezoelectric transducer and the current reference circuit.

12. The self-powered sensor of claim 11 wherein the startup circuit is operable to receive a voltage signal and to cause the reference circuit to generate a stable reference current.

13. The self-powered sensor of claim 9 wherein each channel circuit is further comprised of a current copier operable to receive the reference circuit and to supply the triggering circuit and the switch with the reference current.

14. The self-powered sensor of claim 1 wherein the piezoelectric transducer is operably coupled to a medical implant, such that the voltage signal is generated by the piezoelectric transducer when the piezoelectric transducer experiences a change in strain.

15. The self-powered sensor of claim 14 wherein the total charge stored the non-volatile memory corresponds to the amount of time the rate of strain exceeds a predefined threshold.

16. A self-powered sensor comprising:

a piezoelectric transducer operable to produce a voltage signal corresponding to a change of rate of strain exerted on the piezoelectric transducer;

a startup circuit operable to receive the voltage signal produced by the piezoelectric transducer and to supply a current to a reference circuit;

the reference circuit operable to receive a current from the startup circuit, to generate a stable reference current and to mirror and supply the reference current to an impact monitoring circuit;

the impact monitoring circuit comprising a plurality of impact monitoring channel circuits, each impact monitoring channel circuit sensitive to a predefined frequency corresponding to a rate of change in the voltage signal;

each impact monitoring channel circuit operable to supply the reference current to a corresponding floating gate injector when the impact monitor channel circuit senses a frequency exceeding the predetermined frequency threshold; and each floating gate injector operable to inject charge into a floating gate transistor while the frequency of the voltage signal exceeds the predefined frequency threshold.

17. The self-powered sensor of claim 16 wherein each impact monitoring channel circuit further comprises a triggering circuit and a switch, the triggering circuit operable to drive the switch when the frequency of the voltage signal exceeds the predefined frequency threshold.

18. The self-powered sensor of claim 17 wherein the triggering circuit further comprises a high-pass filter operable to detect a frequency of the voltage signal that exceeds the predefined frequency threshold and operable to bias the gate of a common-source amplifier, the common-source amplifier operable to drive the switch when the gate of the common-source amplifier is biased.

19. The self-powered sensor of 18 wherein the impact monitoring channel circuit further comprises a first current copier and a second current copier;

the first current copier operable to receive the reference current and to supply the reference current to the common source amplifier;

the second current copier operable to receive the reference current and to supply the reference current to the floating gate injector.

20. The self-powered sensor of 18 further comprising a plurality of voltage nodes, each node corresponding to a impact rate channel circuit and each node having a charge corresponding to the charged stored in a capacitor in the floating gate capacitor.

21. A self-powered device for gathering statistics on strain rate comprising:

a transducer operable to generate a voltage signal in response to mechanical stress;

a non-volatile memory comprised of at least one floating gate transistor;

a reference circuit configured to receive the voltage signal having a rate of change from the transducer and operable to generate a current;

an impact impact monitoring circuit configured to receive the voltage signal from the transducer and to receive the current from the reference circuit, the impact monitoring circuit operates to inject the current into the non-volatile memory when the rate of change of the voltage signal exceeds a predetermined threshold.

22. The self-powered device of claim 21 wherein the impact rate monitoring circuit further comprises a switch interposed between the reference circuit and the non-volatile memory, and a triggering circuit that controls the switch based on the rate of change of the voltage signal.

23. The self-powered device of claim 22 wherein the triggering circuit further comprises a high pass filter operably coupled to a transistor, wherein the transistor drives the switch based on the voltage signal passed by the high pass filter.

24. The self-powered device of claim 23 wherein the switch is further defined as a transistor.

25. The self-powered device of claim 21 wherein said device is operable to interface with an RFID chip, whereby statistics relating to strain may be uploaded by a user.

* * * * *

UNITED STATES PATENT AND TRADEMARK OFFICE
CERTIFICATE OF CORRECTION

| | | |
|---|---|---|
| PATENT NO. | : 7,757,565 B2 | |
| APPLICATION NO. | : 12/273844 | |
| DATED | : July 20, 2010 | |
| INVENTOR(S) | : Shantanu Chakrabartty | |

It is certified that error appears in the above-identified patent and that said Letters Patent is hereby corrected as shown below:

Column 2, line 6, after "would", insert --be--.

Column 2, line 57, after "of", delete "a".

Column 3, line 61, after "signal", insert --.--.

Column 4, line 40, "$V_8$" should be --$V_g$--.

Column 6, line 42, "show" should be --shown--.

Column 8, line 56, "32" should be --=--.

Column 11, line 35, "some" should be --same--.

Column 12, line 22, "<<" should be -->>--.

Column 12, line 63, Claim 1, after "memory", insert --;--.

Column 14, line 32, Claim 19, after "of", insert --claim--.

Column 14, line 41, Claim 20, after "of", insert --claim--.

Column 14, line 44, Claim 20, "charged" should be --charge--.

Signed and Sealed this
Twenty-second Day of March, 2011

David J. Kappos
*Director of the United States Patent and Trademark Office*